(12) United States Patent
Ramage et al.

(10) Patent No.: US 7,541,339 B2
(45) Date of Patent: Jun. 2, 2009

(54) PAR-2-ACTIVATING PEPTIDE DERIVATIVE AND PHARMACEUTICAL COMPOSITION USING THE SAME

(75) Inventors: Robert Ramage, Lothian (GB); Robin Plevin, Strathclyde (GB); Kevin Thomas Shaw, Lothian (GB); Lu Jiang, Dallan (CN); Louise Claire Young, Strathclyde (GB); Alan Lang Harvey, Strathclyde (GB); Pu Wang, Edinburgh (GB); Toru Kanke, Musashino (JP); Junichi Kawagoe, Kawagoe (JP); Mototsugu Kabeya, Higashimurayama (JP)

(73) Assignees: The University of Edinburgh, Lothian (GB); The University of Strathclyde, Strathclyde (GB); Kowa Company, Ltd., Aichi (JP)

( * ) Notice: Subject to any disclaimer, the term of this patent is extended or adjusted under 35 U.S.C. 154(b) by 879 days.

(21) Appl. No.: 10/517,803

(22) PCT Filed: Jun. 10, 2003

(86) PCT No.: PCT/JP03/07333

§ 371 (c)(1),
(2), (4) Date: Dec. 10, 2004

(87) PCT Pub. No.: WO03/104268

PCT Pub. Date: Dec. 18, 2003

(65) Prior Publication Data

US 2005/0222384 A1    Oct. 6, 2005

(30) Foreign Application Priority Data

Jun. 10, 2002  (GB) .................. 0213286.8

(51) Int. Cl.
*A61K 38/08*   (2006.01)
*C07K 7/06*    (2006.01)
(52) U.S. Cl. ..................... 514/17; 530/330
(58) Field of Classification Search .......... None
See application file for complete search history.

(56) References Cited

U.S. PATENT DOCUMENTS

2003/0138388 A1 * 7/2003 Seiberg et al. ............. 424/63
2003/0203849 A1 * 10/2003 Araki et al. ................ 514/17

FOREIGN PATENT DOCUMENTS

| WO | WO-97/25351 | 7/1997 |
| WO | WO-00/63371 | 10/2000 |
| WO | WO-01/47556 A1 | 7/2001 |
| WO | WO 01/47556 A1 * | 7/2001 |
| WO | WO-01/62291 A1 | 8/2001 |
| WO | WO-02/056916 A2 | 7/2002 |

OTHER PUBLICATIONS

D'Alessio et al., Bioorganic & Medicinal Chemistry, 7:389-394 (1999).
Santagada et al., Bioorganic & Medicinal Chemistry Letters, 12:21-24 (2002).
Maryanoff et al., Archives of Biochemistry and Biophysics, 386(2):195-204 (2001).
Ferrell et al., "The Journ. Of Clinic. Invest.", vol. 111, No. 1, pp. 35-41 (2003).

* cited by examiner

*Primary Examiner*—Jeffrey E Russel
(74) *Attorney, Agent, or Firm*—Edwards Angell Palmer & Dodge LLP; Peter F. Corless

(57) ABSTRACT

The present invention relates to a peptide derivative represented by the general formula (I) or a salt thereof: $Z\text{-}(CH_2)_n\text{-}CO\text{-}NH\text{-}Leu\text{-}Ile\text{-}Gly\text{-}AA_1\text{-}AA_2\text{-}CO\text{-}R$ (I) wherein Z represents an aryl group which may or may not have a substituent or a heteroaryl group which may or may not have a substituent; n represents 0, 1 or 2; $AA_1\text{-}AA_2$ represents Lys-Val or Arg-Leu; and R represents —OH or —$NH_2$, and relates to a pharmaceutical composition comprising a peptide derivative represented by the general formula (I) or a salt thereof, and a pharmaceutically acceptable carrier thereof. The peptide derivative is useful as a prophylactic and therapeutic agent of dysfunction of masticatory, dysphagia, dysgeusia, ozostomia, intra-oral cavity dysphoria, intra-oral cavity infections, intra-oral cavity inflammations, dry eye, ectocornea detachment, keratitis, corneal ulcer, conjunctivitis, stomach ulcer, duodenal ulcer, gastritis, diarrhea, enteritis or Sjogren's syndrome.

7 Claims, No Drawings

US 7,541,339 B2

PAR-2-ACTIVATING PEPTIDE DERIVATIVE AND PHARMACEUTICAL COMPOSITION USING THE SAME

FIELD OF THE INVENTION

The present invention relates to a peptide derivative with a PAR-2-activating action or a salt thereof, and a pharmaceutical composition comprising the same as the effective ingredient. More specifically, the invention relates to a PAR-2-activating agent. Still more specifically, the invention relates to a prophylactic and therapeutic agent of the decrease of lacrimal fluid secretion, the decrease of saliva secretion or gastrointestinal diseases.

BACKGROUND OF THE INVENTION

PAR (Protease-activated receptor)-2 is one of the PARs belonging to 7-transmembrane G-protein-coupled receptor family.

Four types of PARs namely PAR-1, PAR-2, PAR-3 and PAR-4 have been cloned so far and these belong to a receptor family mediating the actions of serine proteases such as thrombin and trypsin in various cells. The functions of PAR-1, PAR-2, PAR-3 and PAR-4 have been elucidated as receptors involved in platelet aggregation via thrombin. Structurally or from the standpoint of activation mechanism, PAR-2 has numerous properties common to other PARs. Functionally, however, PAR-2 is never activated by thrombin but is activated by trypsin and tryptase.

A specific site in the N-terminal amino acid sequences of these PARs is cleaved by thrombin or such proteases. Peptide fragments generated by the cleavage bind to the binding site of receptors thereof of themselves to activate the receptors. The amino acid sequences activating the PARs are summarized and expressed according to the one character amino acid expression as below.

| PAR-1: | SFLLRN-NH$_2$ | (human) | (SEQ ID NO: 1) |
|---|---|---|---|
| PAR-2: | SLIGKV-NH$_2$ | (human) | (SEQ ID NO: 2) |
|  | SLIGRL-NH$_2$ | (mouse) | (SEQ ID NO: 3) |
| PAR-3: | None |  |  |
| PAR-4: | GYPGQV | (human) | (SEQ ID NO: 4) |
|  | GYPGKF | (mouse) | (SEQ ID NO: 5) |

PAR-1, PAR-2 and PAR-4 can be activated non-enzymatically by exogenously-added peptides with the amino acid sequences of the peptide fragments generated via the cleavage but PAR-3 cannot be activated by such exogenously-added peptides. Recent research works have verified that mouse PAR-3 is the cofactor of PAR-4 since PAR-3 per se is never activated but is activated in the co-presence of PAR-4 (Nature, 404, 609-613 (2000)).

Cloning of PAR-2 was done in 1994 by Nystedt (Proc. Natl. Acad. Sci. USA, 91, 9208-9212 (1994)). It is known that PAR-2 is activated by tissue factors Factor VIIa and Factor Xa, acrosin as one of sperm proteases, trypsin-like serine protease identified in rat brain, trypsin, tryptase and synthetic peptides of similar sequences as those of PAR-2 ligands (Pharmacological Rev, 53, 245-282, 2001; Br. J. Pharmacol. 1998, 123, 1434-1440).

Furthermore, some PAR-2-activating agents have been reported, which have higher activity than the activity of a partial PAR-2 amino acid sequence (SLIGKV) (SEQ ID NO: 2) activating human PAR-2 and include trans-cinnamoyl-LIGRL-O-NH$_2$ (SEQ ID NO: 6) found by Hollenberg et al. (Br. J. Pharmacol. 1998, 123, 1434-1440) (PNAS, 95, 7766-7771 (1998); BJP, 125, 1445-1454 (1998)).

A report also tells that pharmaceutical agents containing a PAR-2-activating agent as the effective ingredient are useful for the prophylaxis and therapeutic treatment of the decrease of saliva secretion, the decrease of lacrimal fluid secretion or gastrointestinal diseases (Japanese Patent Laid-open Nos. 064203/2001, 181208/2001 and 233790/2001).

However, compounds already reported as PAR-2 agonists are not satisfactory in terms of biological properties, physicochemical properties, and ready synthesis. Therefore, further examinations have been needed for the development of such PAR-2 agonists into pharmaceutical products.

SUMMARY OF THE INVENTION

The invention provides a compound with an excellent PAR-2-activating action and a pharmaceutical composition comprising the same as the effective ingredient.

In such circumstances, the present inventors have made intensive investigations. Consequently, the inventors have found that a peptide derivative represented by the general formula (I) has a higher activity than the activity of the partial PAR-2 amino acid sequence (SLIGKV) (SEQ ID NO: 2) activating human PAR-2 and is useful as a pharmaceutical agent for the prophylaxis and therapeutic treatment of the decrease of lacrimal fluid secretion, the decrease of saliva secretion or gastrointestinal diseases. Thus, the invention has been achieved.

More specifically, the invention relates to a peptide derivative represented by the general formula (I) or a salt thereof:

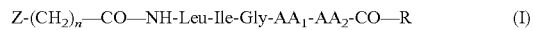

$$Z\text{-}(CH_2)_n\text{---}CO\text{---}NH\text{-}Leu\text{-}Ile\text{-}Gly\text{-}AA_1\text{-}AA_2\text{-}CO\text{---}R \qquad (I)$$

wherein Z represents an aryl group which may or may not have a substituent or a heteroaryl group which may or may not have a substituent; n represents 0, 1 or 2; AA$_1$-AA$_2$ represents Lys-Val or Arg-Leu; and R represents —OH or —NH$_2$.

Additionally, the invention relates to a pharmaceutical composition comprising a peptide derivative represented by the general formula (I) or a salt thereof, and a pharmaceutically acceptable carrier thereof.

PREFERRED EMBODIMENTS OF THE INVENTION

The peptide derivative of the invention is represented by the general formula (I), where the aryl group as Z is a carbon cyclic group of mono-ring type, multi-ring type or condensed ring type, with 6 to 30 carbon atoms, preferably 6 to 14 carbon atoms, specifically including for example phenyl group and naphthyl group, preferably. The heteroaryl group as Z is a hetero-cyclic group of 5- to 7-membered mono-ring type, multi-ring type or condensed ring type, the group containing at least one to 3 nitrogen atoms, oxygen atoms or sulfur atoms within the ring and specifically including for example furyl group, thienyl group, pyridyl group or quinolyl group, preferably.

The aryl group or heteroaryl group as Z may or may not have a substituent, which includes but is not limited to any aryl group or heteroaryl group with no adverse effects on the activity of the inventive peptide derivative, specifically including for example a halogen atom, a lower alkyl group, a lower alkoxyl group, phenyl group, a phenyl-lower alkyl group, nitro group, amino group, hydroxyl group, and carboxyl group. The halogen atom includes for example chlorine atom, fluorine atom, and bromine atom. The lower alkyl group is preferably a linear or branched lower alkyl group with one to 15 carbon atoms, preferably one to 6 carbon atoms, which includes for example methyl group and ethyl group. The lower alkoxyl group preferably includes a linear or branched lower alkoxyl group with one to 15 carbon atoms, preferably one to 6 carbon atoms, which includes for example methoxyl group and ethoxyl group. The lower alkyl group in the phenyl-lower alkyl group includes alkylene groups including the lower alkyl group, for example methylene group and ethylene group.

Substituents for these lower alkyl group, lower alkoxyl group, phenyl-group, and phenyl-lower alkyl group may additionally be substituted with a halogen atom and the like.

The group Z in the general formula (I) in accordance with the invention includes for example substituted or unsubstituted phenyl group, naphthyl group, furyl group, thienyl group, pyridyl group and quinolyl group, specifically including for example phenyl group, 4-methoxyphenyl group, 3-methoxyphenyl group, 2-methoxyphenyl group, 2,4-dimethoxyphenyl group, 3,5-dimethoxyphenyl group, 4-phenethylphenyl group, 3-phenethylphenyl group, 2-phenethylphenyl group, 4-nitrophenyl group, 3-nitrophenyl group, 2-nitrophenyl group, 2,4-dinitrophenyl group, 3,4-dinitrophenyl group, 4-methylphenyl group, 3-methylphenyl group, 2-methylphenyl group, 2,4-dimethylphenyl group, 3,5-dimethylphenyl group, 4-fluorophenyl group, 3-fluorophenyl group, 2-fluorophenyl group, 2,4-difluorophenyl group, 3,5-difluorophenyl group, 2,4,5-trifluorophenyl group, 4-phenylphenyl group, 3-phenylphenyl group, 2-phenylphenyl group, 2-furyl group, 3-furyl group, 5-methoxy-2-furyl group, 5-methyl-2-furyl group, 1-naphthyl group, 2-naphthyl group, 4-methoxy-1-naphthyl group, 4-methyl-1-naphthyl group, 4-methoxy-2-naphthyl group, 4-methyl-2-naphthyl group, 4-pyridyl group, 2-pyridyl group, 3-pyridyl group, 2-methyl-4-pyridyl group, 4-methyl-2-pyridyl group, 2-thienyl group, 3-thienyl group, 3-methyl-2-thienyl group, 4-methyl-2-thienyl group, 4-methyl-3-thienyl group, 6-quinolyl group, 7-quinolyl group, 8-quinolyl group, 4-quinolyl group, 4-methyl-6-quinolyl group and the like.

In the general formula (I), in accordance with the invention, n represents 0, 1 or 2 and the group with the inferior letter "n" is bound to the group Z. When n is 0, the group Z is directly bound to carbonyl group; when n is 1, the group z is bound through methylene group to carbonyl group; and when n is 2, the group Z is bound through ethylene group to carbonyl group.

R in the general formula (I) represents —OH or —NH$_2$, or the salt thereof.

In accordance with the invention, $AA_1$-$AA_2$ in the general formula (I) represents two types of amino acids bound together. The amino acid $AA_1$ is preferably Lys or Arg, while $AA_2$ is preferably Val or Leu. $AA_1$ and $AA_2$ are bound together in the sequence $AA_1$-$AA_2$ along the N-terminal to C-terminal direction. Preferable $AA_1$-$AA_2$ includes Lys-Val or Arg-Leu.

The C terminus of the peptide derivative represented by the general formula (I) of the invention is preferably free, but may satisfactorily be esterified or amidated or may form a salt for formulation. The salt of the peptide derivative represented by the general formula (I) in accordance with the invention can be selected from pharmaceutically acceptable salts. For example, the salt can be a salt with an inorganic base or an organic base. The inorganic salt includes for example a salt with an alkali metal such as sodium or potassium, an alkali earth metal such as calcium or magnesium, aluminum salt and ammonium salt. The organic salt includes for example a salt with primary amines such as methylamine, ethylamine and ethanolamine, secondary amines such as diethylamine, diethanolamine, dicyclohexylamine, and N,N'-dibenzylethylenediamine, and tertiary amines such as trimethylamine, triethylamine, pyridine, picoline, and triethanolamine. Additionally, the salt may be a salt with basic amino acids such as arginine, lysine and ornithine.

PAR-2 activation with the peptide derivative represented by the general formula (I) in accordance with the invention can be tested by various known methods. For example, the Hollenberg's method (Hollenberg, M. D., et al., *Can. J. Physiol. Pharmacol.*, 75, 832-841 (1997)), the Kawabata's method (Kawabata, A., et al., *J. Pharmacol. Exp. Ther.*, 288, 358-370 (1999)) and the Hawthorne's method (Howthorne et al., A High-Throughput Microtiter Plate-Based Calcium Assay for the Study of Protease-Activated Receptor 2 Activation, Analytical Biochemistry 290, 378-379 (2001)) may be used for the test.

The inventors tested the PAR-2 activation potency according to the modified Hawthorne's method. In brief, that is the assay of the calcium mobilization in cells endogenously expressing human PAR-2. In this assay, cells were loaded with Fluorescent Ca2+ indicator dye in presence of Probenecid, an inhibitor of anion exchange transporter, and stimulated with agonists. The agonist-mediated intracellular calcium mobilization was measured using multiwell plate reader.

The method is illustrated more specifically as follows.

Human colorectal adenocarcinoma cell line, HCT-15, expressing endogenous PAR-2 at high levels were seeded in 96-well black wall clear bottom plates and subconfluent cells were loaded with Fluorescent Ca2+ indicator dye (Calcium Plus Assay Reagent, Molecular Devices) in serum free medium (RPMI) containing 2.5 mM Probenecid and incubated for 1 hr at 37 C. Then cells were stimulated with various concentrations of test compounds and fluorescent change was determined at wave length of 485 nm for excitation and 525 nm for emission (Cutoff 515 nm) using multiwell scanning fluorometer (FlexStation, Molecular Devices).

SLIGKV-OH (SEQ ID NO: 2) as a known PAR-2 activation peptide was used as a comparative compound, and the results are shown below in Table 1.

TABLE 1

| Compound (Example No.) | MW (measured) | Agonist Activity (EC50, μM) |
|---|---|---|
| SLIGKV-OH | — | 22.83 +/− 13.91 |
| Example 6 | 623.5 | 1.68 +/− 0.36 |
| Example 16 | 622.2 | 0.32 +/− 0.06 |
| Example 17 | 664.4 | 0.25 +/− 0.13 |
| Example 18 | 665.0 | 1.21 +/− 0.60 |

Consequently, it was shown that 2-furylcarbonyl derivative shown below in Example 6, 16, 17 and 18 (the group Z-(CH$_2$)$_n$— is 2-furyl group in the general formula (I)) were at an EC$_{50}$ value about 1/14-fold, 1/71-fold, 1/91-fold and 1/19-fold, respectively that of the comparative peptide. Additionally, other peptide derivatives of the invention had activation potencies about 2-fold and over that of the comparative peptide.

The peptide derivative of the invention can be prepared by various other synthetic methods of related art or methods according to such methods, with no specific limitation. For example, the peptide derivative can be prepared at the following reaction method.

Following the amino acid sequence of an intended peptide by general peptide-bond-forming reactions by liquid phase process or solid phase process, the peptide derivative of the invention can be prepared through a route of sequentially binding together individual amino acids one by one or a route of binding together individual fragments of several amino acids preliminarily synthesized. For peptide-bond formation, various known methods can be applied, namely a method for converting the C-terminal carboxyl group of an amino acid or a peptide into a reactive functional group, or a method for using general condensation agents. Examples of the reactive derivatives of amino acid or peptide include halogenated acids such as acid chloride, azidated acids, symmetric acid anhydrides, mix acid anhydrides with pivalic acid, and activated esters such as p-nitrophenyl ester. Examples of the condensing agent include 1,3-dicyclohexylcarbodiimide, 1-cyclohexyl-3-morpholinoethylcarbodiimide, 1-(3-diaminopropyl)-3-ethylcarbodiimide, 1,1'-carbonyldiimidazole, diethylphosphate cyanide, diphenylphosphoryl azide, bis(2-oxo-3-oxazolidine)phosphinyl chloride, and 2-chloro-1-methylpyridinium iodide.

For these reactions, if necessary, an appropriate base or an appropriate solvent may be used. The base includes for example organic bases such as pyridine, triethylamine, and diisopropylethylamine; or inorganic bases such as sodium carbonate and sodium hydrogen carbonate. The solvent includes for example dimethylformamide, tetrahydrofuran, dioxane, acetonitrile, methylene chloride and dichloroethane.

When using a condensing agent such as 1,3-dichlorohexylcarbodiimide, appropriate activating agents such as 1-hydroxybenzotriazole and N-hydroxysuccinimide can accelerate the reaction velocity when added, effectively, to suppress racemization. Various reagents listed herein may be used in forms bound to resins such as polystyrene, so as to simplify the isolation procedure of the peptide synthetic ally prepared.

During the peptide-bond-forming reaction, further, functional groups that should never be involved in the reaction because of their potential side effects are preferably protected. The protective group of the amino group includes for example benzyloxycarbonyl, t-butoxycarbonyl, allyloxycarbonyl, 9-fluorenylmethoxycarbonyl, p-methoxybenzyloxycarbonyl, 3-nitro-2-pyridinesulphenyl, trifluoroacetyl, phthaloyl, and formyl. The protective group of the carboxyl group includes for example methyl ester, ethyl ester, and benzyl ester. Additionally, the protective group of the guanidyl group in arginine includes for example p-toluenesulfonyl, nitro, benzyloxycarbonyl, and 4-methoxy-2,3,6-trimethylbenzenesulfonyl.

Depending on the property of each of these protective groups, the protective groups can be eliminated by acid treatment, base treatment, reduction, hydrolysis and the like. Acids including for example hydrogen chloride, hydrogen fluoride, methanesulfonic acid, trifluoromethanesulfonic acid, trifluoroacetic acid, trimethylsilane bromide, trimethylsilyltrifluoromethanesulfonate, tetrafluoroboric acid, and boron bromide can be used as the acid. The base includes for example piperidine, pyrrolidine, triethylamine, and diisopropylethylamine. Additionally, the reduction conditions include the use of sodium/liquid ammonia, palladium catalyst/hydrogen, palladium catalyst/formic acid and the like. For the hydrolysis, lithium hydroxide and sodium hydroxide can be used.

The N-terminal acyl group in the peptide derivative of the invention may be modified into N-acylated leucine via the reaction between the corresponding carboxylic acid or a reactive derivative and leucine of which the functional groups that should not be involved in the reaction are protected. The resulting N-acylated leucine may be used for the peptide synthesis. Otherwise, after the synthesis of the object peptide or during the synthetic process, the amino group in leucine is similarly acylated. The conditions for the peptide-bond-forming reaction are applicable to the reaction conditions then.

The compound of the invention as recovered by the method can be purified if necessary by general methods, for example gel chromatography, partition chromatography, ion exchange chromatography, affinity chromatography, countercurrent distribution chromatography, high performance liquid chromatography with various carriers, and recrystallization.

Due to the PAR-2-activating action, the peptide derivative represented by the general formula (I) in accordance with the invention has an action to promote lacrimal fluid secretion, an action to promote saliva secretion, an action to suppress gastric juice secretion, an action to promote mucus secretion, and an action to protect mucosal membrane. Thus, the peptide derivative is useful as a prophylactic and therapeutic agent of dysfunction of masticatory, dysphagia, dysgeusia, ozostomia, intra-oral cavity dysphoria, intra-oral cavity infections, intra-oral cavity inflammations, dry eye, ectocornea detachment, keratitis, corneal ulcer, conjunctivitis, stomach ulcer, duodenal ulcer, gastritis, diarrhea, enteritis or Sjogren's syndrome.

The pharmaceutical composition of the invention contains the peptide derivative represented by the general formula (I) of the invention or a salt thereof, and a pharmaceutically acceptable carrier thereof. The pharmaceutically acceptable carrier includes various additives for general pharmaceutical use. For example, the pharmaceutically acceptable carrier includes solubilizers, excipients, binders and diluents. The pharmaceutical composition of the invention can be formulated into various dosage forms, using these carriers. The pharmaceutical composition of the invention can be formulated into dosage forms, for example, tablets, capsules, granules, powders, lotions, ointments, injections and suppositories.

Additionally, the pharmaceutical composition of the invention can be prepared by known methods. For the formulation of oral dosage forms, for example, an appropriate combination of the following additives may be used for formulation; solubilizers such as gum tragacanth, gum arabic, sucrose ester, lecithin, olive oil, soybean oil, and PEG400; excipients such as starch, mannitol, and lactose; binders such as sodium carboxymethylcellulose, and hydroxypropyl cellulose; disintegrators such as crystal cellulose and carboxymethylcellulose calcium; lubricants such as talc and magnesium stearate; and fluidity-enhancing agents such as light anhydrous silicic acid.

The pharmaceutical composition of the invention can be administered orally or parenterally. For example, the pharmaceutical composition can be administered by intravenous injection, trans-mucosal dosing, trans-dermal dosing, intramuscular dosing, subcutaneous dosing and intra-rectal dosing.

The dose of the pharmaceutical composition of the invention varies, depending on the body weight, age, sex and symptom of a patient and the like. On a basis of the effective ingredient peptide derivative represented by the general formula (I) of the invention, the pharmaceutical composition is generally administered at a dose of the peptide derivative of 0.01 to 1,000 mg, preferably 0.1 to 100 mg in one portion or three-dividend portions per day per adult.

All the contents described in the British priority application No. 0231286.8 filed on Jun. 10, 2002 are incorporated in the present application.

EXAMPLES

The invention will now be described more specifically in the following Examples. But the technical scope of the invention is not limited to these Examples.

Example 1

SEQ ID NO: 7 Preparation for

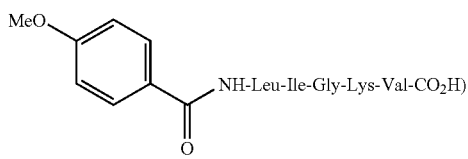

(1) Loading of Resin:

Fmoc-Val-OH (6 eq.) was dissolved in DMF and 1,3-diisopropylcarbodiimide (3 eq.) was added. The mixture was sonicated for 10 min and added to Wang-resin (0.1 mmol), which was swollen in DMF and catalytic amount of DMAP (30 mg) added. The resin mixture was then sonicated for 2 h at room temperature. Loading was 0.37 mmol/g.

(2) Peptide Chain Assembly:

The peptide chain was synthesized on an ABI430 peptide synthesizer. 1,3-diisopropylcarbodiimide/HOCt were used as coupling reagents. Single coupling cycles were applied and the deprotection of each cycle was monitored by UV at 302 nm.

(3) Coupling of 4-methoxybenzoic Acid to the Peptide:

After the deprotection of the last amino acid, the resin was removed from the synthesizer, washed with DMF/dichloromethane, and dried. 4-methoxybenzoic acid (5 eq.) was dissolved in dichloromethane and triphosgene (6 eq.) was added. The mixture was stirred for 30 min at 0° C. and added to the peptide resin without further purification. N,N-Diisopropylethylamine (10 eq.) was added to the mixture and it was sonicated for 1 h at room temperature. The reaction mixture was filtered off and the resin was washed with DMF/dichloromethane and dried.

(4) Cleavage and Purification:

The peptoid was cleaved with 90% TFA/H$_2$O and purified by HPLC [Column: Vydac C18 (250×22 mm); Solvent system: A (0.1% TFA/H$_2$O), B (0.1% TFA/CH$_3$CN), 10-50% B over 30 min; Flow rate: 5 mL/min; Detection: UV at 214 nm]. Analytical HPLC [Column: Vydac C18 (250×10 mm); Solvent system: A (0.1% TFA/H$_2$O), B1(0.1% TFA/CH$_3$CN), 10-90% B over 30 min; Flow rate: 1 mL/min; Detection: UV at 214 nm] was used to check the purity and electrospray MS was used for identification. The title compound was in >95% purity according to HPLC.

Retention time: 19.8 min

MS (m/z): 663.4 (required 662.83)

Example 2

Preparation for

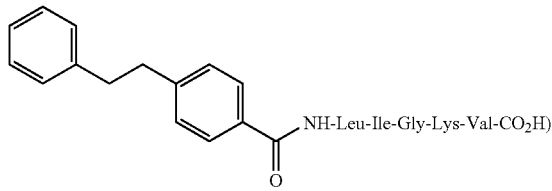

The title compound was prepared in the same manner as in Example 1 except that 4-phenethylbenzoic acid was used instead of 4-methoxybenzoic acid as the acid to be coupled.

Retention time: 23.4 min

MS (m/z): 737.5 (required 736.96)

Example 3

Preparation for

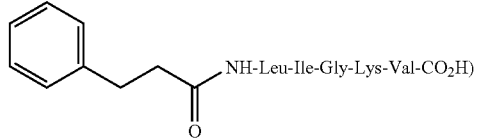

The title compound was prepared in the same manner as in Example 1 except that 3-phenylpropionic, acid was used instead of 4-methoxybenzoic acid as the acid to be coupled.

Retention time: 25.1 min

MS (m/z): 661.6 (required 660.86)

Example 4

Preparation for

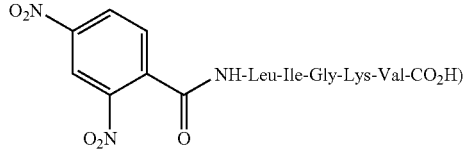

The title compound was prepared in the same manner as in Example 1 except that 2,4-dinitrobenzoic acid was used instead of 4-methoxybenzoic acid as the acid to be coupled.

Retention time: 19.7 min

MS (m/z): 723.5 (required 722.80)

Example 5

Preparation for

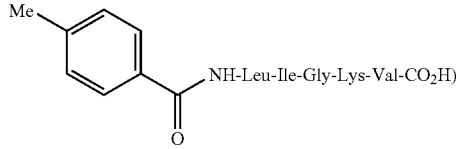

The title compound was prepared in the same manner as in Example 1 except that 4-methylbenzoic acid was used instead of 4-methoxybenzoic acid as the acid to be coupled.

Retention time: 20.6 min

MS (m/z): 647.5 (required 646.83)

Example 6

Preparation for

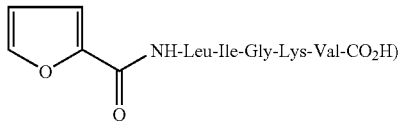

The title compound was prepared in the same manner as in Example 1 except that 2-furancarboxylic acid was used instead of 4-methoxybenzoic acid as the acid to be coupled.
Retention time: 24.2 min
MS (m/z): 623.5 (required 622.76)

Example 7

Preparation for

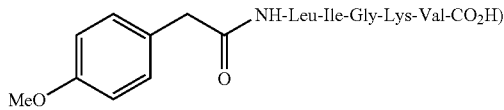

The title compound was prepared in the same manner as in Example 1 except that 2-(4-methoxyphenyl)acetic acid was used instead of 4-methoxybenzoic acid as the acid to be coupled.
Retention time: 23.7 min
MS (m/z): 678.5 (required 676.86)

Example 8

Preparation for

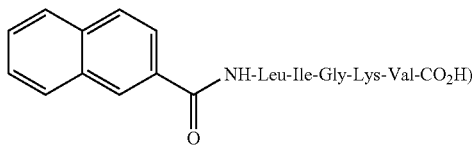

The title compound was prepared in the same manner as in Example 1 except that 2-naphthalenecarboxylic acid was used instead of 4-methoxybenzoic acid as the acid to be coupled.
Retention time: 26.0 min
MS (m/z): 683.2 (required 682.86)

Example 9

Preparation for

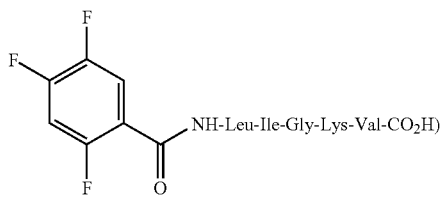

The title compound was prepared in the same manner as in Example 1 except that 2,4,5-trifluorobenzoic acid was used instead of 4-methoxybenzoic acid as the acid to be coupled.
Retention time: 20.6 min
MS (m/z): 687.9 (required 686.78)

Example 10

Preparation for

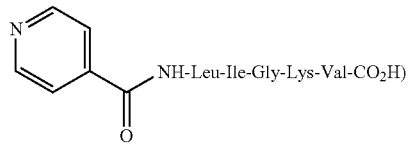

The title compound was prepared in the same manner as in Example 1 except that 4-pyridinecarboxylic acid was used instead of 4-methoxybenzoic acid as the acid to be coupled.
Retention time: 14.4 min
MS (m/z): 634.5 (required 633.79)

Example 11

Preparation for

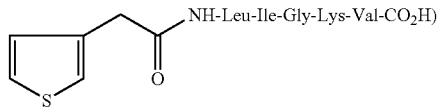

The title compound was prepared in the same manner as in Example 1 except that 2-(3-thienyl)acetic acid was used instead of 4-methoxybenzoic acid as the acid to be coupled.
Retention time: 19.0 min
MS (m/z): 653.6 (required 652.86)

Example 12

Preparation for

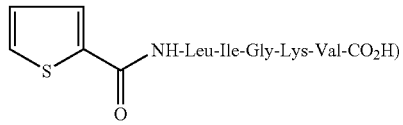

The title compound was prepared in the same manner as in Example 1 except that 2-thiophenecarboxylic acid was used instead of 4-methoxybenzoic acid as the acid to be coupled.
Retention time: 21.0 min
MS (m/z): 639.6 (required 638.82)

Example 13

Preparation for

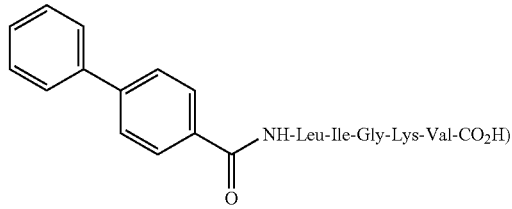

The title compound was prepared in the same manner as in Example 1 except that 4-phenylbenzoic acid was used instead of 4-methoxybenzoic acid as the acid to be coupled.
Retention time: 23.2 min
MS (m/z): 709.4 (required 708.91)

Example 14

Preparation for

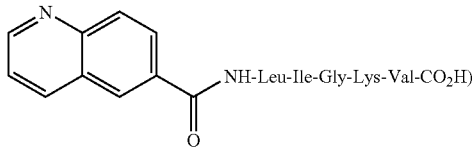

The title compound was prepared in the same manner as in Example 1 except that 6-quinolinecarboxylic acid was used instead of 4-methoxybenzoic acid as the acid to be coupled.
Retention time: 17.3 min
MS (m/z): 684.4 (required 683.87)

Example 15

Preparation for

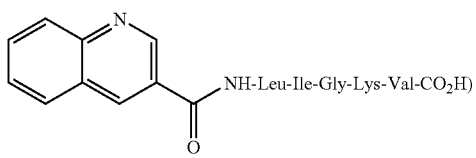

The title compound was prepared in the same manner as in Example 1 except that 3-quinolinecarboxylic acid was used instead of 4-methoxybenzoic acid as the acid to be coupled.
MS (m/z): 683.5 (required 683.87)

Example 16

Preparation for

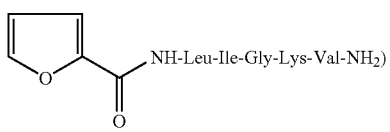

The title compound was prepared using Methylbenzhydrylamine resin (MBHA resin). All procedures except for cleavage from the resin were same as described in Example 6. Cleavage from the resin were conducted at 0° C. with liquid HF in the presence of anisole as a carvocation scavenger.
Retention time: 19.3 min
MS (m/z): 622.2 (required 621.8)

Example 17

Preparation

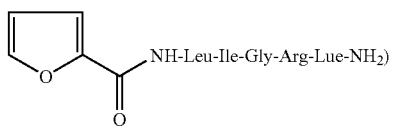

The title compound (SEQ ID NO: 6) was prepared in the same manner as in Example 16 except that Arginine and Leucine was used respectively instead of Lysine and Valine as the amino acid to be coupled.
Retention time: 21.1 min
MS (m/z): 664.4 (required 663.8)

Example 18

Preparation for

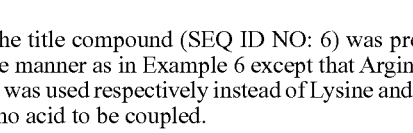

The title compound (SEQ ID NO: 6) was prepared in the same manner as in Example 6 except that Arginine and Leucine was used respectively instead of Lysine and Valine as the amino acid to be coupled.
Analytical HPLC [Column; Inertsil ODS-3V (4.6×150 mm); solvent system; $CH_3CN/0.01\%$ TFA, 30-90% over 30 min; Flow rate 1 mL/min; Detection; UV at 214 nm]
Retention time: 4.38 min
MS (m/z): 665.0 (required 664.8)

---

The invention claimed is:

1. A peptide derivative represented by the general formula (I) or a salt thereof:

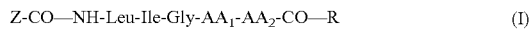

wherein Z represents a furyl group; $AA_1$-$AA_2$ represents Lys-Val or Arg-Leu; and R represents —OH or —$NH_2$.

2. A pharmaceutical composition comprising a peptide derivative or a salt thereof according to claim 1, and a pharmaceutically acceptable carrier thereof.

3. The pharmaceutical composition according to claim 2, which is a PAR-2-activating agent.

4. A method of treating a patient suffering from or susceptible to decrease of saliva secretion, decrease of lacrimal fluid secretion or gastrointestinal disorder, comprising administering to the patient a peptide derivative or a salt thereof according to claim 1.

5. The method of claim 4 wherein a patient is identified as suffering from decrease of saliva secretion, decrease of lacrimal fluid secretion or gastrointestinal disorder and the peptide derivative or a salt thereof is administered to the identified patient.

6. A method of treating a patient suffering from or susceptible to dysfunction of masticatory, dysphagia, (taste disorder), ozostomia, intra-oral cavity dysphoria, intra-oral cavity infection, intra-oral cavity inflammation, dry eye, ectocornea detachment, keratitis, corneal ulcer, conjunctivitis, stomach ulcer, duodenal ulcer, gastritis, diarrhea, or enteritis comprising:

administering to the patient a peptide derivative or a salt thereof according to claim 1.

7. The method of claim 6 wherein the patient is identified as suffering from dysfunction of masticatory, dysphagia, dysgeusia (taste disorder), ozostomia, intra-oral cavity dysphoria, intra-oral cavity infection, intra-oral cavity inflammation, dry eye, ectocornea detachment, keratitis, corneal ulcer, conjunctivitis, stomach ulcer, duodenal ulcer, gastritis, diarrhea, or enteritis and the peptide derivative or a salt thereof is administered to the identified patient.

* * * * *

SEQUENCE LISTING

<160> NUMBER OF SEQ ID NOS: 7

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Phe Leu Leu Arg Asn
 1               5

```
<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Leu Ile Gly Lys Val
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Leu Ile Gly Arg Leu
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Pro Gly Gln Val
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Tyr Pro Gly Lys Phe
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Ile Gly Arg Leu
  1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
                          -continued
<400> SEQUENCE: 7

Leu Ile Gly Lys Val
 1               5
```